United States Patent [19]

Leonard et al.

[11] Patent Number: 4,735,775

[45] Date of Patent: Apr. 5, 1988

[54] MASS TRANSFER DEVICE HAVING A HEAT-EXCHANGER

[75] Inventors: Ronald J. Leonard, Harvard; Kenneth M. Johnson; Thomas L. Drehobl, both of Lindenhurst, all of Ill.

[73] Assignee: Baxter Travenol Laboratories, Inc., Deerfield, Ill.

[21] Appl. No.: 908,968

[22] Filed: Sep. 17, 1986

Related U.S. Application Data

[63] Continuation of Ser. No. 583,853, Feb. 27, 1984, abandoned.

[51] Int. Cl.[4] .......................... A61M 1/18; A61M 1/36; B01D 13/01; F28F 1/08
[52] U.S. Cl. ................................ 422/46; 128/DIG. 3; 165/179; 210/321.78
[58] Field of Search ............... 165/154, 156, 177, 179, 165/184; 422/46, 45, 48; 210/180, 181, 182, 321.4; 128/399, 400, DIG. 3

[56] References Cited

U.S. PATENT DOCUMENTS

| | | | |
|---|---|---|---|
| 2,152,280 | 3/1939 | Rapuano | 165/154 |
| 3,034,769 | 5/1962 | Bertin et al. | |
| 3,109,485 | 11/1963 | Fortier | |
| 3,205,147 | 9/1965 | Foure et al. | |
| 3,326,280 | 6/1967 | Bosquain et al. | 165/161 |
| 3,468,631 | 9/1969 | Raible et al. | 128/400 |
| 3,579,810 | 5/1971 | Mon | 422/45 |
| 3,731,731 | 5/1973 | Kyvsgaard et al. | 165/46 |
| 3,764,271 | 10/1973 | Brumfeld | |
| 3,839,204 | 10/1974 | Ingenito et al. | 422/46 |
| 3,968,834 | 7/1976 | Mangus et al. | 165/68 |
| 4,085,730 | 4/1978 | Severson et al. | |
| 4,108,242 | 8/1978 | Searight et al. | |
| 4,201,195 | 5/1980 | Sakhuja | |
| 4,216,825 | 8/1980 | Sumitomo | |
| 4,312,757 | 1/1982 | Brumfield | |

FOREIGN PATENT DOCUMENTS

0108525  5/1984  European Pat. Off.
3025623  2/1982  Fed. Rep. of Germany.

Primary Examiner—Barry S. Richman
Assistant Examiner—C. M. Delahunty
Attorney, Agent, or Firm—Kay H. Pierce; Paul C. Flattery; George H. Gerstman

[57] ABSTRACT

A heat exchanger (38) is provided which may be used in a mass transfer device (20), such asn an oxygenator or a dialyzer. The heat exchanger comprises a core (40) formed of a corrugated metal having a high thermal conductivity. Each of the corrugations of the core comprises substantially parallel side walls (70, 72). A first fluid, such as blood, is introduced onto the outside of the core. A second fluid, such as water, is introduced into the inside of the core. The first and second fluids will be in heat exchange relationship with each other and the flow of the fluids is substantially uniform resulting from the substantially parallel side walls of the corrugations. The core is formed by providing a flexible metalhose, annealing the flexible metal hose, compressing the annealed hose and expanding the compressed hose to a length that is substantially less than its original length but greater than its length during compression.

5 Claims, 6 Drawing Sheets

MASS TRANSFER DEVICE HAVING A HEAT-EXCHANGER

This application is a continuation of application Ser. No. 583,853, filed Feb. 27, 1984, now abandoned.

TECHNICAL FIELD

The present invention concerns a novel heat exchanger and a novel method for making the heat exchanger. The heat exchanger of the illustrative embodiment may be used with a mass transfer device, such as an oxygenator or a dialyzer, and it may be enclosed within the mass transfer device housing.

BACKGROUND ART

Mass transfer devices, such as oxygenators and dialyzers, are known in which the mass transfer device housing encloses a heat exchanger for controlling the temperature of the blood. For example, a combination blood oxygenator and heat exchanger is disclosed in U.S. Pat. No. 3,764,271.

Although the heat exchanger of the present invention may be used in many different fields, and although no limitation is intended, for simplicity the heat exchanger of the present invention will be described herein as being used in a blood oxygenator. Disposable blood oxygenators are widely used today in connection with the oxygenation of a patient's blood, and the present invention is ideally suited for this field of use, among others.

It is desirable that a disposable blood oxygenator be relatively compact, have a low prime volume, be easy to manufacture, and have a relatively low cost. It is important that a heat exchanger, used in connection with a disposable blood oxygenator, enable substantially uniform flow of the fluids that will be in heat exchange relationship with each other. It is also desirable that the oxygenator and heat exchanger be formed as a single unit, that the heat exchanger be positioned close to the oxygenating medium, such as the oxygenator fiber bundle, and that the heat exchanger have high efficiency with a relatively low pressure drop.

The present invention provides a heat exchanger having the characteristics and abilities set forth above.

DISCLOSURE OF THE INVENTION

In accordance with the present invention, a heat exchanger is provided which comprises a core having an inside and an outside and formed of a corrugated metal having a high thermal conductivity. Each of the corrugations of the core comprises an outer wall, a contiguous first side wall, a contiguous inner wall, and a contiguous second side wall. The first and second side walls are substantially parallel to each other and a plurality of the corrugations repeat contiguously. A first fluid, such as blood, is introduced onto the outside of the core. A second fluid, such as water, is introduced into the inside of the core. The first and second fluids are in heat exchange relationship with each other and the flow of the fluids is substantially uniform resulting from the substantially parallel first and second side walls of the corrugations.

In the illustrative embodiment, the core is formed by the steps of providing a flexible metal hose, annealing the flexible metal hose, compressing the annealed hose and expanding the compressed hose to a length that is substantially less than its original length but greater than its length during compression. These steps have been found to provide the substantial parallelism of the walls of the corrugations, enabling substantially uniform flow of the fluids.

In the illustrative embodiment, the second fluid flows through a manifold which is located within the inside of the core. The manifold comprises a generally S-shaped cross-sectional configuration. The S-shape is defined by an intermediate wall having opposed ends with a first curved member extending from one end toward the other end but spaced therefrom to form a first slot, and with the second curved member extending from the other end and toward the one end but spaced therefrom to form a second slot. The second fluid is introduced into the first chamber defined by one side of the intermediate wall and the first curved member. In this manner, the second fluid will exit from the second chamber defined by the opposite side of the intermediate wall and the second curved member.

In the illustrative embodiment, a mass transfer device is provided in which the device has a housing enclosing a mass transfer medium and a spaced heat exchanger. The mass transfer medium is operative to enable mass transfer between a first fluid, such as blood, and a third fluid, such as oxygen. The mass transfer device includes the aforesaid heat exchanger and means are provided for conveying the first fluid, such as blood, that has been through the heat exchanger, from the heat exchanger to one area of the mass transfer medium. The third fluid, such as oxygen, is introduced to another area of the mass transfer medium to enable mass transfer to occur.

In one embodiment of the invention, the second fluid manifold which is provided and which is located within the inside of the core comprises a first chamber defined by a first member, and a second chamber defined by a second member. The second fluid is first introduced into the first chamber and the second fluid is then directed from the first chamber to the second chamber. Means are provided for creating turbulent flow of the second fluid as it exits from the first chamber. In an illustrative embodiment, the first member and second member define openings between the first chamber and the second chamber. A screen member is located between the first chamber and the second chamber.

In accordance with the present invention, a process is provided for making a heat exchanger. The process comprises the steps of providing a flexible metal hose, annealing the flexible metal hose, thereafter compressing the annealed hose, and thereafter expanding the compressed hose to a length that is substantially less than its original length but greater than its length during compression.

A more detailed explanation of the invention is provided in the following description and claims, and is illustrated in the accompanying drawings.

DETAILED DESCRIPTION OF THE ILLUSTRATIVE EMBODIMENT

Referring to the drawings, a heat exchanger constructed in accordance with the principles of the present invention is disclosed therein, used in a blood oxygenator environment. In the perspective view of FIG. 1, partially broken for clarity, oxygenator 20 includes a molded plastic housing 22 with a first fluid inlet 24 for use as a blood inlet, a first fluid outlet 26 for use as a blood outlet, a second fluid inlet 28 which operates as a water inlet, a second fluid outlet 30 which operates as a water outlet, a third fluid inlet 32 which operates as an oxygen inlet, and a third fluid outlet 34 which operates as an oxygen outlet. Housing 22 has a lower portion 36 which encloses the heat exchanger 38.

Figure 5:
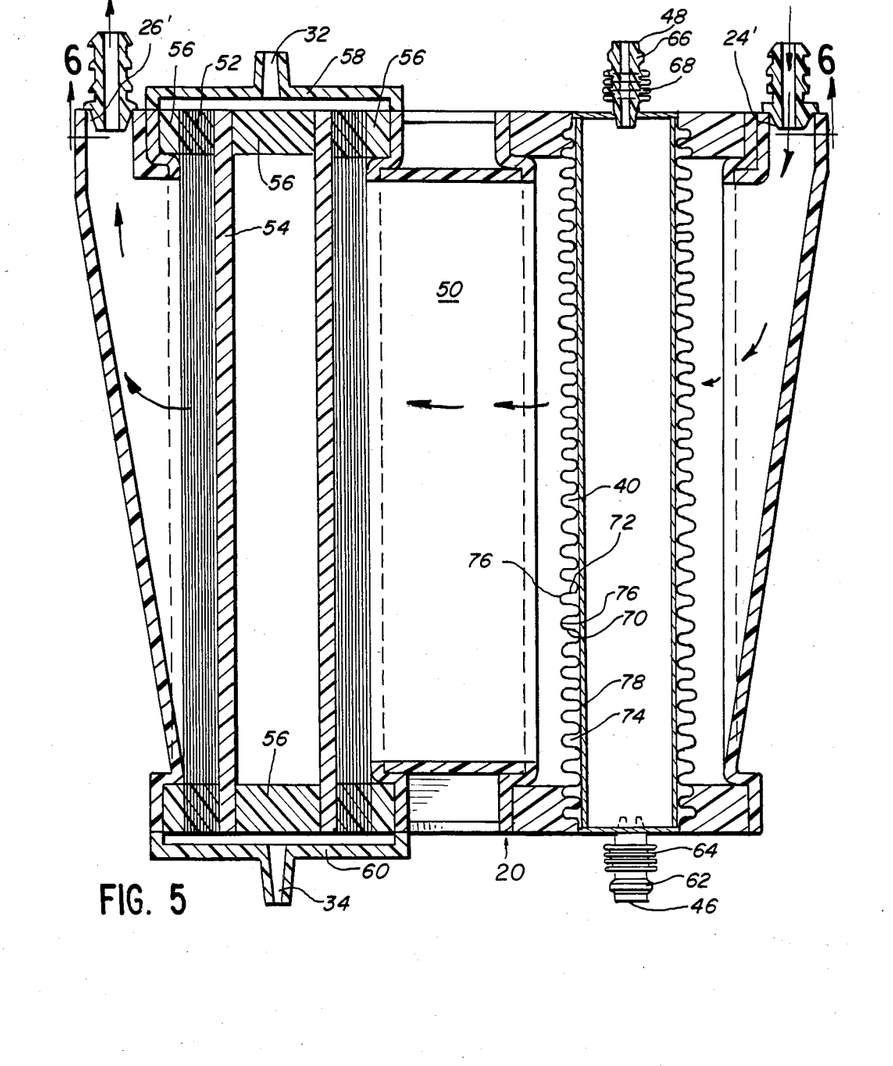
FIG. 5 is a cross-sectional elevation of a slightly modified mass transfer device.
Figure 6:
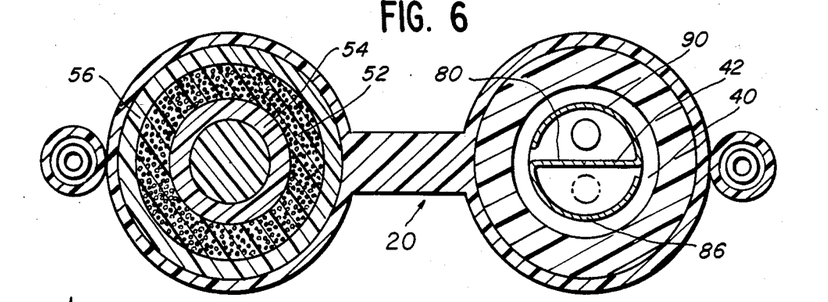
FIG. 6 is a cross-sectional view of the mass transfer device of FIG. 5, taken along the plane of the line 6—6 of FIG. 5.

Referring to FIGS. 1-6, heat exchanger 38 includes a core 40, a manifold 42, end caps 44, inlet port 46 and outlet port 48. In FIGS. 5 and 6, an oxygenator 20' is illustrated. Oxygenator 20' is similar to oxygenator 20 of FIG. 1, but the blood inlet 24' and the blood outlet 26' are at the top of the oxygenator instead of being at the side of the oxygenator as in FIG. 1.

Figure 1:
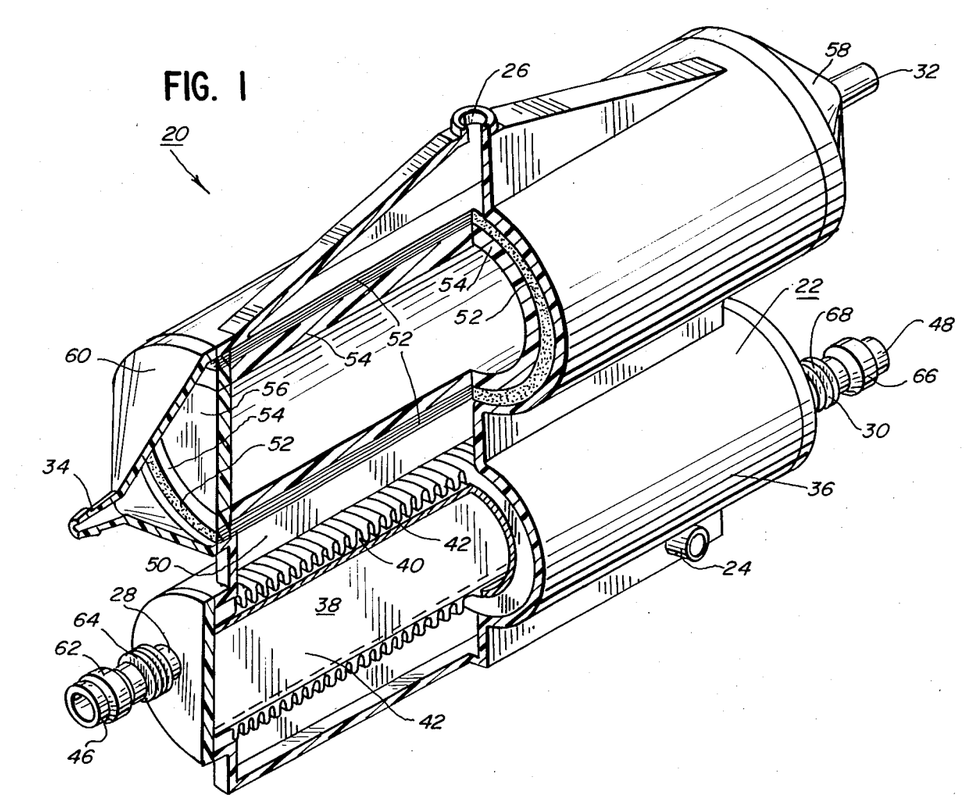
FIG. 1 is a perspective view, partially broken for clarity, of a mass transfer device constructed in accordance with the principles of the present invention.

As illustrated most clearly in FIGS. 1 and 5, a passageway 50 couples the heat exchanger 38 with the outside of a mass transfer medium 52. In the illustrative embodiment, mass transfer medium 52 comprises a hollow fiber bundle in tubular form as is well known in the art, wound about a plastic core 54. The hollow fiber bundle 52 is encapsulated at its ends by means of a potting compound 56, although the ends of the hollow fibers are open to form oxygen flow paths as is known in the art. Housing end caps 58 and 60 secure the ends of the mass transfer device assembly.

The blood path is into inlet 24, around the outside of heat exchanger 38, then around the hollow fiber bundle 52 and out of outlet 26. The cooling and/or heating water flows via inlet port 46 into inlet 28, through manifold 42 and inside the heat exchanger core 40, and out outlet 30 and outlet port 48. The oxygen flows into inlet 32, the fiber bundle and out the outlet 34.

To enable the inlet water hose (not shown) and the outlet water hose (not shown) to be connected to inlet port 46 and outlet port 48, respectively, more effectively, and to alleviate spillage, a snap-on coupling 62 and a corrugated portion 64 is formed with inlet port 46. Snap-on portion 62 enables the water hose to be snapped onto inlet port 46 and corrugations 64 enable the inlet port 46 to be bent for ease in connection and handling. Likewise, outlet port 48 is formed with snap-on portion 66 and with corrugations 68 to enable an outlet hose to be quick-coupled to outlet port 48 and to enable the outlet port 48 to bend for ease in connection and handling.

The heat exchanger core 40 of the present invention is novel and has been found to be effective to enable substantially uniform flow of the fluids that will be in heat exchange relationship with each other. A construction of heat exchanger core 40 and its method of manufacture are explained as follows, with particular reference to FIGS. 7–8.

The heat exchanger core 40 is formed from a high pressure flexible metal hose, of the type that is often sold in auto parts stores for use as the flexible metal hose for conveying cooling fluid within the engine compartment. In the illustrative embodiment, the outer diameter of the flexible hose is 2 inches and the inner diameter is 1.5 inches. Typically, this flexible metal hose is corrugated, with approximately six corrugations per inch.

A broken, enlarged diagrammatic view of portion of this flexible metal hose is presented in FIG. 8a. Referring to FIG. 8a, it can be seen that the side walls 70, 72 of each corrugation are not parallel to each other. It should be noted that FIGS. 8a to 8b are not to scale and are diagrammatic only.

Figure 7:
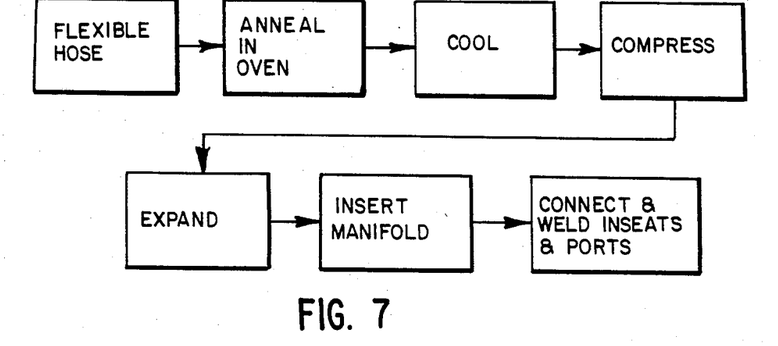
FIG. 7 is a flow chart of the steps comprising a process of making a heat exchanger core.
Figure 8A:
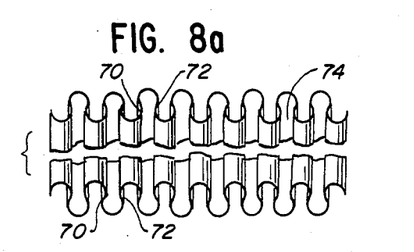
FIG. 8a is a diagrammatic view of a cross-section of a high pressure flexible hose, without showing the metal thickness.
Figure 8B:
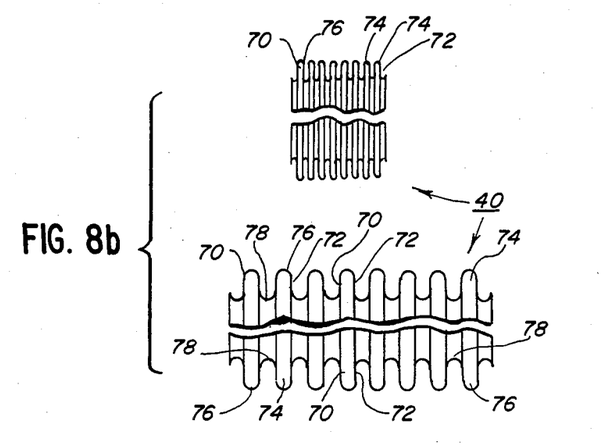
FIG. 8b is a diagrammatic view of a cross-section of a heat exchanger core that has been constructed from the FIG. 8a hose, with the bottom portion of FIG. 8b being a greatly enlarged section of the top portion of FIG. 8b.

The steps for forming heat exchanger core 40 are illustrated in FIG. 7. The flexible hose as described above is provided, and it is annealed in an oven. The annealed hose is allowed to cool and is then compressed to between 5 percent and 25 percent of its original length, preferably about 20 percent of its original length. Thereafter the opposite ends are pulled apart so that it is expanded to 1.5 times to 3 times its compressed length, preferably about 2 times its compressed length. Manifold 42 is then inserted into the heat exchanger core and thereafter the end caps and ports are connected and welded to form the resulting heat exchanger illustrated in FIG. 4.

As the flexible metal hose is compressed, side walls 70, 72 are still curvilinear and are not parallel to each other. This will prevent the desirable uniform flow because the flow will favor the more open areas and there will be unsuitable flow in the relatively closed areas. The flexible hose is compressed to about 20 percent of its original length, but flow becomes even more restricted because of the hairpin-type configuration. However, we have discovered that after compression, when the flexible hose is expanded to 1.5 times to 3 times its compressed length, preferably 2 times its compressed length, the side walls 70, 72 become substantially parallel with each other, providing more constant volume with substantially uniform flow. Referring to FIG. 8b, it can be seen that the resulting heat exchanger core comprises a plurality of contiguous corrugations 74, with each of the corrugations having an outer wall 76, a contiguous first side wall 70, a contiguous inner wall 78, and a contiguous second side wall 72, with the first side wall 70 and the second side wall 72 being substantially parallel to each other.

In the illustrative embodiment, the length of the original flexible hose was 22 inches and it had approximately 6 corrugations per inch. This flexible metal hose is formed of a non-corrosive substance such as stainless steel or aluminum having a high thermal conductivity, and it was subjected to annealing in an oven at approximately 1000° F. The annealed hose was then removed from the oven, air cooled and then compressed to a length of 4 inches, in which it had approximately 33 corrugations per inch. The compressed metal hose was then expanded so that its length became 7.5 inches having approximately 18 corrugations per inch. The expanded metal hose may have between about 12 and about 22 corrugations.

Figure 2:
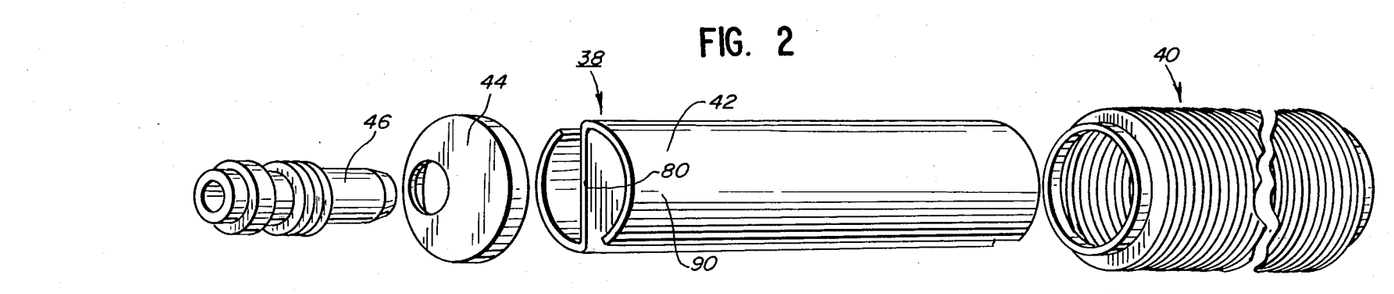
FIG. 2 is an exploded perspective view of the heat exchanger used in the mass transfer device of FIG. 1.
Figure 3:
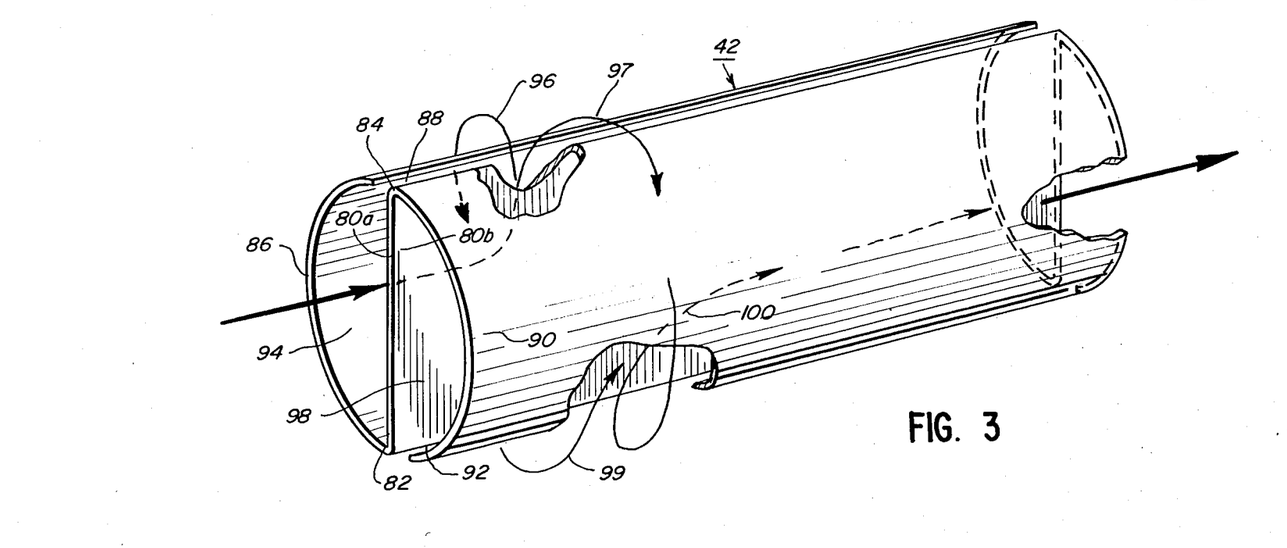
FIG. 3 is a perspective diagrammatic view of a fluid manifold used in the heat exchanger of FIG. 2.
Figure 4:
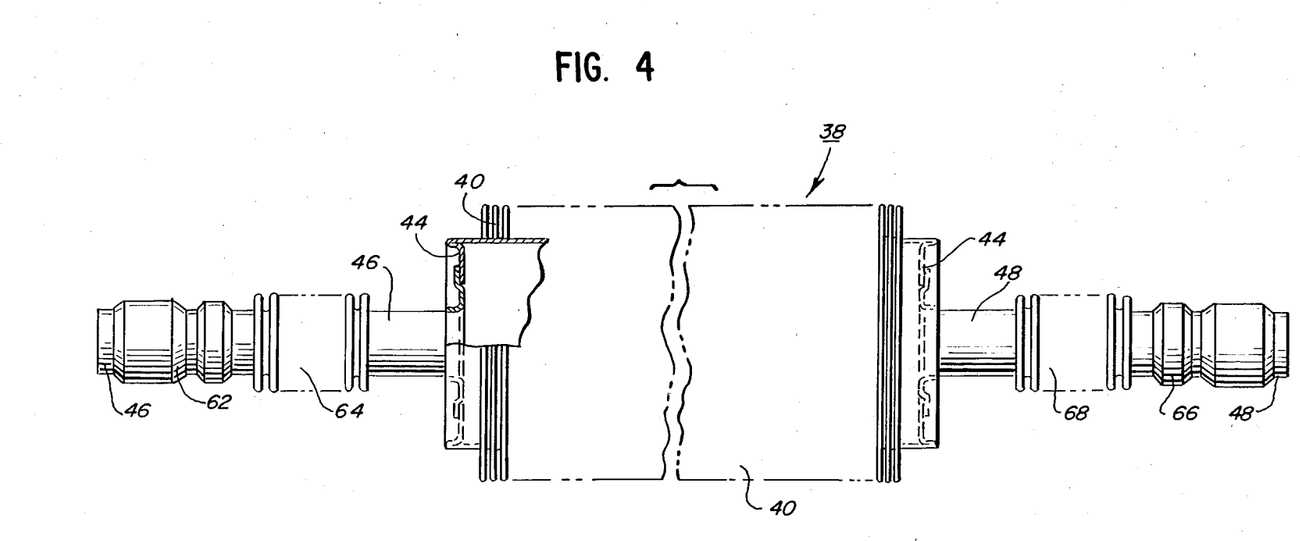
FIG. 4 is an elevational view, partially shown in phantom for simplicity, of a heat exchanger constructed in accordance with the principles of the present invention.

Referring to FIGS. 2 and 3, the manifold 42 which is inserted into heat exchanger core 40 is illustrated therein. Manifold 42 operates to distribute the second fluid which flows from inlet 28 to outlet 30 (FIG. 1). Manifold 42 has a generally S-shaped cross sectional configuration, with the S-shape being defined by an intermediate wall 80 having opposed ends 82, 84. A first curved member 86 extends from end 82 and toward the other end 84 but spaced therefrom to form a first longitudinal slot 88. A second curved member 90 extends from end 84 and toward end 82 but is spaced therefrom to form a second longitudinal slot 92. The second fluid, i.e., water, is introduced into a first chamber 94 defined by one side 80a of intermediate wall 80 and the first curved member 94. The second fluid will flow in chamber 94, out of slot 88, around curved members 86 and 90 in the direction of arrows 96, 97, through slot 92 and into chamber 98 in the direction of arrows 99, 100, through chamber 98 and out of chamber 98. Chamber 98 is defined by side 80b of intermediate member 80 and curved member 90.

It can be seen that the cooling or heating water will flow on the inside of heat exchanger core 40 and the blood will flow on the outside thereof. The blood that has been heat exchanged will then flow into the mass transfer area where it will be oxygenated with the oxygenated blood exiting via blood outlet 26.

In another form of the invention, device for providing turbulent flow is utilized. Heat transfer in turbulent flow is significantly greater than heat transfer in laminar fluid flow, due to the turbulence induced mixing. To this end, a turbulence inducer is illustrated in FIGS. 9-11, which turbulence inducer is intended to achieve greater overall heat transfer.

Figure 9:
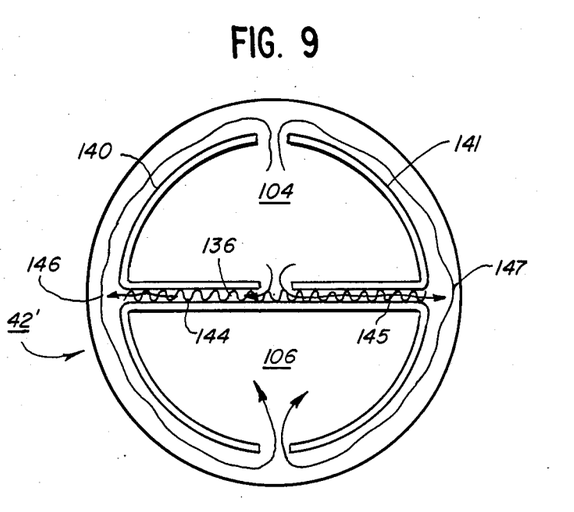
FIG. 9 is an end view of a fluid manifold for the heat exchanger of the present invention, according to another form of the invention, and showing with arrowed lines the fluid flow.
Figures 10, 11:
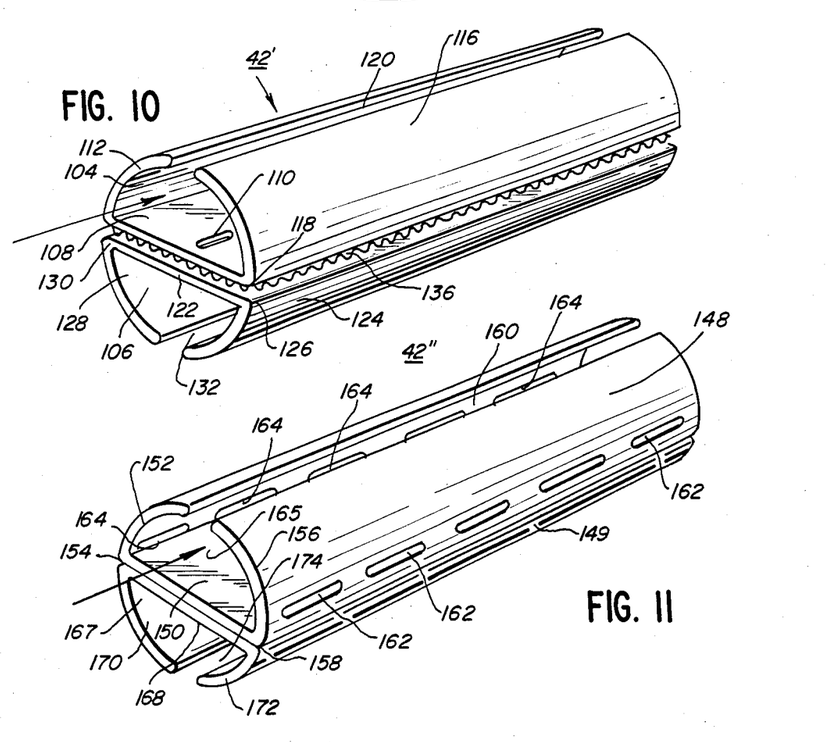
FIG. 10 is a perspective view of the manifold of FIG. 9.
FIG. 11 is a perspective view of an alternative manifold.

Referring to FIGS. 9 and 10, a manifold 42' is shown therein comprising a first chamber 104 and a second chamber 106. The first chamber is defined by a first member having a planar base 108 defining a series of collinear spaced slots 110. Although not all of the slots are illustrated, in the embodiment of FIGS. 9 and 10, there may be between four and ten slots 110. A first curved member 112 extends from end 114 of base 108 and a second curved member 116 extends from end 118 of base 108. Curved members 112 and 116 extend toward each other but are spaced from each other to define a longitudinal slot 120.

The second chamber 106 is defined by a second base member 122 having a third curved member 124 extending from end 126 thereof. A fourth curved member 128 extends from end 130 of base 122, with third and fourth curved members 124 and 128 extending toward each other, but being spaced from each other to define a longitudinal slot 132. Slot 132 is on the opposite side of manifold 42' from slot 120, and the cross-sectional configuration of curved members 112, 116, 124 and 128 is substantially circular. A screen 136 is interposed between base 108 and base 122 to aid in creating the turbulent flow desired. Manifold 42' is inserted into heat exchanger core 40, in the same manner that manifold 42 (FIG. 2) is inserted into heat exchanger core 40. Water inlet 28 (FIG. 1) will introduce the entry water to chamber 104 and most of the water will flow via slot 120, around the outside of the manifold (i.e., inside the heat exchanger core) in the direction of arrowed lines 140, 141, through slit 132 and into chamber 106, and out the end of chamber 106 opposite to the entry end of chamber 104. Some of the water will flow through slots 110 and pass through screen 136 in the direction of arrowed flow lines 144, 145. This water will enter the flow at about points 146 and 147 (FIG. 9) to enter the flow stream at substantially a right angle, to create turbulence.

In FIG. 11, a manifold 42'' is illustrated, and it includes an upper member 148 comprising a base 150, a first curved member 152 extending from one end 154 of base 150 and a second curved member 156 extending from end 158 of base 150. Curved members 152 and 156 curve toward each other but are spaced to form a longitudinal slot 160. As illustrated, a series of collinear slots 162 are defined by second curved member 156 toward the junction between curved member 156 and base 150. Likewise, first curved member 152 defines a plurality of collinear slots 164 adjacent the junction between first curved member 152 and base 150. The upper member 148 illustrated in FIG. 11 defines a first chamber 165. A second chamber 167 is defined by a connected lower member 149 including base 168, third curved member 170 and fourth curved member 172. Curved members 170 and 172 curve toward each other and are spaced to form a slot 174.

The water will flow into the first chamber 165 defined by the upper member 148 with some of the water flowing up through slot 160 and around the outside of the manifold, then back into slot 174 and out the second chamber 167. Some of the water from the first chamber 165 will flow through slots 162 and 164 to enter the outside flow at an angle to the flow stream to create turbulence.

A disposable blood oxygenator has been disclosed that is relatively compact, has a low prime volume, is easy to manufacture and has a relatively low cost. The heat exchanger in accordance with the present invention enables substantially uniform flow of the fluid that will be in heat exchange relationship with each other.

Although illustrative embodiments of the invention have been shown and desribed, it is to be understood that various modifications and substitutions may be made by those skilled in the art without departing from the novel spirit and scope of the present invention.

What is claimed is:

1. A mass transfer device comprising:
   a housing having an upper hollow portion and a lower hollow portion, said lower hollow portion being in flow communication with said upper hollow portion;
   a mass transfer means located within said upper hollow portion of said housing, said mass transfer means having an inner surface and an outer surface;
   a heat exchanger located within said lower hollow portion of said housing, said heat exchanger comprising a core having an inner surface and an outer surface, said core being made from a generally cylindrical piece of corrugated metal of substantially constant thickness constructed and arranged to provide a plurality of corrugations, each of said corrugations having an outer wall, an integral first side wall, an integral inner wall, and an integral second side wall, said first and second integrgal side walls being substantially parallel to each other;

a fluid manifold disposed within said core of said heat exchanger, said fluid manifold defining a first longitudinal slot communicating said fluid manifold with the inside of said core and a second longitudinal slot communicating said fluid manifold with the inside of said core, with the first and second slots being on opposed sides of the manifold, said manifold having an intermediate wall which defines a first manifold chamber communicating with the first slot and a second manifold chamber communicating with a second slot;

a first fluid outlet projecting from said upper hollow portion of said housing and in fluid communication with said outer surface of said mass transfer means;

a first fluid inlet projecting from said lower hollow portion of said housing, said first fluid inlet being in fluid communication with said outer surface of said core of said heat exchanger, said first fluid inlet and first fluid outlet being positioned to define a flow path therebetween via said outer surfaces of said core and said mass transfer means;

a second fluid outlet projecting from said lower hollow porton of said housing;

a second fluid inlet projecting from said lower hollow portion of said housing, said second fluid inlet and said second fluid outlet being in fluid communication with said inner surface of said core of said heat exchanger;

said fluid manifold being configured so that a second fluid will move via said second fluid inlet into said first manifold chamber, through said first slot, around the outside of the fluid manifold into said second slot, out from said second manifold chamber and out of said heat exchanger via said second fluid outlet;

a third fluid outlet projecting from said upper hollow portion of said housing; and a third fluid inlet projecting from said upper hollow portion of said housing, said third fluid inlet and said third fluid outlet being in fluid communication with said inner surface of said mass transfer means.

2. The mass transfer device recited in claim 1 wherein said second fluid inlet and said second fluid outlet are provided with corrugated portions to permit manual flexing thereof.

3. The mass transfer device recited in claim 1 wherein said core of said heat exchanger has between about 12 and about 22 said corrugations per inch.

4. The mass transfer device recited in claim 1 wherein said mass transfer means comprises a fiber bundle.

5. The mass transfer device recited in claim 1, wherein said mass transfer means comprises an oxygenator, said first fluid outlet is a blood outlet, said first fluid inlet is a blood inlet, said second fluid outlet is a water outlet, said second fluid inlet is a water inlet, said third fluid outlet is an oxygen outlet, and said third fluid inlet is an oxygen inlet.

* * * * *